US008210026B2

(12) United States Patent
Klee et al.

(10) Patent No.: US 8,210,026 B2
(45) Date of Patent: Jul. 3, 2012

(54) SYSTEM FOR INTEGRATED BACKFLUSH IN A GAS CHROMATOGRAPH

(75) Inventors: Matthew S. Klee, Wilmington, DE (US); Lawrence John Gajdos, Chadds Ford, PA (US); Bruce Douglas Quimby, Lincoln University, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 708 days.

(21) Appl. No.: 12/331,671

(22) Filed: Dec. 10, 2008

(65) Prior Publication Data

US 2010/0139363 A1 Jun. 10, 2010

(51) Int. Cl.
*G01N 30/62* (2006.01)
(52) U.S. Cl. .................. 73/23.27; 73/23.29; 73/23.4
(58) Field of Classification Search .............. 73/23.22, 73/23.27, 23.29, 23.4, 23.41
See application file for complete search history.

(56) References Cited

U.S. PATENT DOCUMENTS

| | | | | | |
|---|---|---|---|---|---|
| 3,800,602 | A | * | 4/1974 | Jones | 73/23.42 |
| 3,858,435 | A | * | 1/1975 | Stevens | 73/23.35 |
| 3,887,280 | A | * | 6/1975 | McLean | 356/316 |
| 3,935,097 | A | * | 1/1976 | Roof | 210/659 |
| 4,038,864 | A | * | 8/1977 | Cooper et al. | 73/23.2 |
| 4,534,207 | A | * | 8/1985 | Szakasits et al. | 73/23.38 |
| 4,766,760 | A | * | 8/1988 | Poshemansky et al. | 73/23.35 |
| 4,814,089 | A | * | 3/1989 | Kumar | 210/659 |
| 4,845,985 | A | * | 7/1989 | Berger | 73/23.25 |
| 4,895,809 | A | * | 1/1990 | Schlabach et al. | 436/518 |
| 4,962,662 | A | * | 10/1990 | Berger | 73/23.42 |
| 4,970,905 | A | * | 11/1990 | McClennen et al. | 73/864.34 |
| 4,971,915 | A | * | 11/1990 | Schwartz et al. | 436/139 |
| 4,982,597 | A | * | 1/1991 | Berger | 73/23.25 |
| 5,191,211 | A | * | 3/1993 | Gorman, Jr. | 250/282 |
| 5,196,169 | A | * | 3/1993 | Schick et al. | 422/81 |
| 5,340,476 | A | * | 8/1994 | Berger et al. | 210/198.2 |
| 5,595,709 | A | * | 1/1997 | Klemp | 422/88 |
| 5,723,091 | A | * | 3/1998 | Welsh | 422/54 |
| 7,383,718 | B2 | * | 6/2008 | McCurry et al. | 73/23.4 |
| 2007/0000828 | A1 | * | 1/2007 | Norman et al. | 210/198.2 |

OTHER PUBLICATIONS

Lin Bingyi and Yao Weijun; Purged Nitrogen-Phosphorus Detector; Agilent Technologies (Shanghai) Co. Ltd.; Apr. 21, 2004.

* cited by examiner

*Primary Examiner* — Daniel Larkin

(57) ABSTRACT

A detector in a gas chromatograph includes a detector inlet configured to receive a chromatographic column, the chromatographic column having a column entrance and a column exit, the column exit coupled to the detector inlet, a restriction integrated within the detector, the restriction located to receive an output of the chromatographic column, at least one pressure regulated gas source provided for normal gas chromatograph operation and arranged to provide at least one gas to a location between the integrated restriction and the column exit, and a backflush controller coupled to the pressure regulated gas source, the backflush controller configured to control a pressure differential between the column exit and the column entrance such that the at least one gas backflushes the chromatographic column when a pressure at the column exit exceeds a pressure at the column entrance.

20 Claims, 10 Drawing Sheets

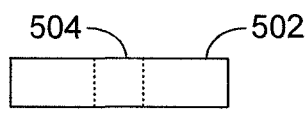
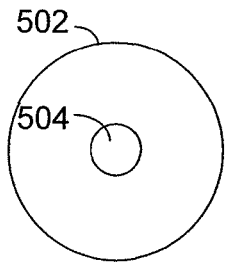
FIG. 6A     FIG. 6B
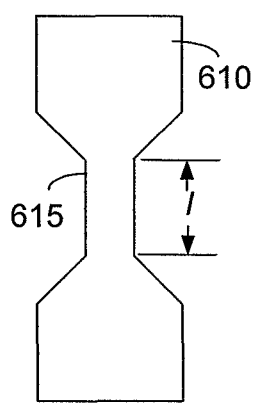
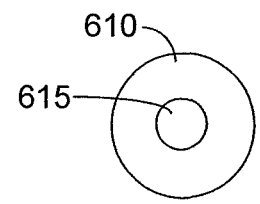
FIG. 7A     FIG. 7B
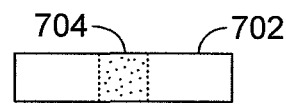
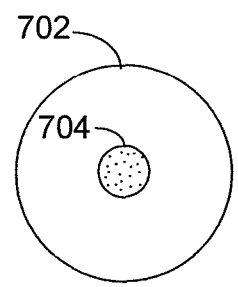
FIG. 8A     FIG. 8B

SYSTEM FOR INTEGRATED BACKFLUSH IN A GAS CHROMATOGRAPH

BACKGROUND

Many chemical analysis applications, such as gas and liquid chromatography, rely on the flow of fluid through one or more tubes and couplings. For example, in gas chromatography, one or more tubes, referred to as columns, are used to analyze a sample of material to determine its components. A chromatographic column can be, for example, a packed column or a capillary column. As the material under analysis flows through the column, the interaction of the material under analysis and the material on the inside of the column results in the constituent components of the material under analysis eluting from the column at different times. This elutant from the column is transferred to a detector. Detector response is indicative of the amount of elutant passing through the detector. In the case of mass spectrometer detectors, the detector can also provide information to help identify the elutant.

During gas chromatography, it is sometimes desirable to cause a gas to flow through the column in a direction opposite the normal direction of flow used during analysis. This is referred to as "backflushing" the column. There are many circumstances in which it is desirable to backflush a chromatographic column. For example, it is desirable to backflush a chromatographic column when analyzing compounds that include highly-retained components that may not elute from the column, thereby contaminating the column and negatively affecting subsequent analyses.

Common backflush techniques rely on the use of additional system components such as pressure control devices, gas supply lines, connection devices, additional columns acting as restrictors, and additional fluid flow components.

FIG. 1 is a schematic diagram illustrating an arrangement for column backflush in an existing gas chromatograph system. The gas chromatograph system 10 includes an inlet pneumatic module 12 coupled to a chromatographic inlet 14. The entrance of the column 16 is connected to the chromatographic inlet 14. A sample (not shown) to be analyzed can be introduced to the column through the chromatographic inlet 14 over connection 13. A gas, which can be referred to as a carrier gas, flows from the inlet pneumatic module 12 through the chromatographic inlet 14 to the column 16. The inlet pneumatic module 12 controls the pressure and flow of the carrier gas to the chromatographic inlet 14 and the column 16, and controls the pressure at the entrance of the column 16. The exit of the column 16 is connected to an intermediate connection device, which, in this example, is illustrated as a purged union 18. The purged union 18 facilitates the connection of the column 16 to an external restriction 24. An auxiliary pneumatic module 22 controls the exit pressure of the column 16, and the flow through the purged union 18. The external restriction 24 is coupled to a detector 26. A detector pneumatic module 28 controls the pneumatic functions of the detector 26.

Although not present during normal chromatographic analysis, the purged union 18, the auxiliary pneumatic module 22 and the external restriction 24 are required so that a backflush flow can be established in the column 16. For normal chromatographic analysis, the exit of the column 16 is directly connected to the detector 26 with no restrictor, no additional pneumatic module, and no purged restrictor. In addition, the process of configuring the system 10 for backflush can take considerable time, requires additional operator training and/or expertise and can represent a significant change in operational procedures.

Therefore, it would be desirable to have the ability to backflush a chromatographic column with minimum additional hardware, expertise, and change to standard operating procedures and practices.

SUMMARY OF THE INVENTION

According to an embodiment, a detector in a gas chromatograph includes a detector inlet configured to receive a chromatographic column, the chromatographic column having a column entrance and a column exit, the column exit coupled to the detector inlet, a restriction integrated within the detector, the restriction located to receive an output of the chromatographic column, at least one pressure regulated gas source provided for normal gas chromatograph operation and arranged to provide at least one gas to a location between the integrated restriction and the column exit, and a backflush controller coupled to the pressure regulated gas source, the backflush controller configured to control a pressure differential between the column exit and the column entrance such that the at least one gas backflushes the chromatographic column when a pressure at the column exit exceeds a pressure at the column entrance.

Other embodiments of the invention will be discussed with reference to the figures and to the detailed description of the preferred embodiments.

BRIEF DESCRIPTION OF THE FIGURES

The invention will be described by way of example, in the description of exemplary embodiments, with particular reference to the accompanying figures.

FIGS. 6A and 6B are schematic diagrams illustrating an embodiment of an integrated restriction element.

FIGS. 7A and 7B are schematic diagrams illustrating an alternative embodiment of a restriction element.

FIGS. 8A and 8B are schematic diagrams illustrating another alternative embodiment of a restriction element.

DETAILED DESCRIPTION

The system for integrated backflush in a gas chromatograph can be implemented in any gas chromatograph that uses a packed column, a capillary column, or any chromatographic column. However, the following description will generally refer to a capillary column.

As used herein, the term flow is intended to include forms of mass flow, programmed mass flow, or volumetric flow and/or forms of linear velocity such as programmed linear velocity, average linear velocity, inlet, outlet, or instantaneous linear velocity through a fluid conduit.

Figure 1:
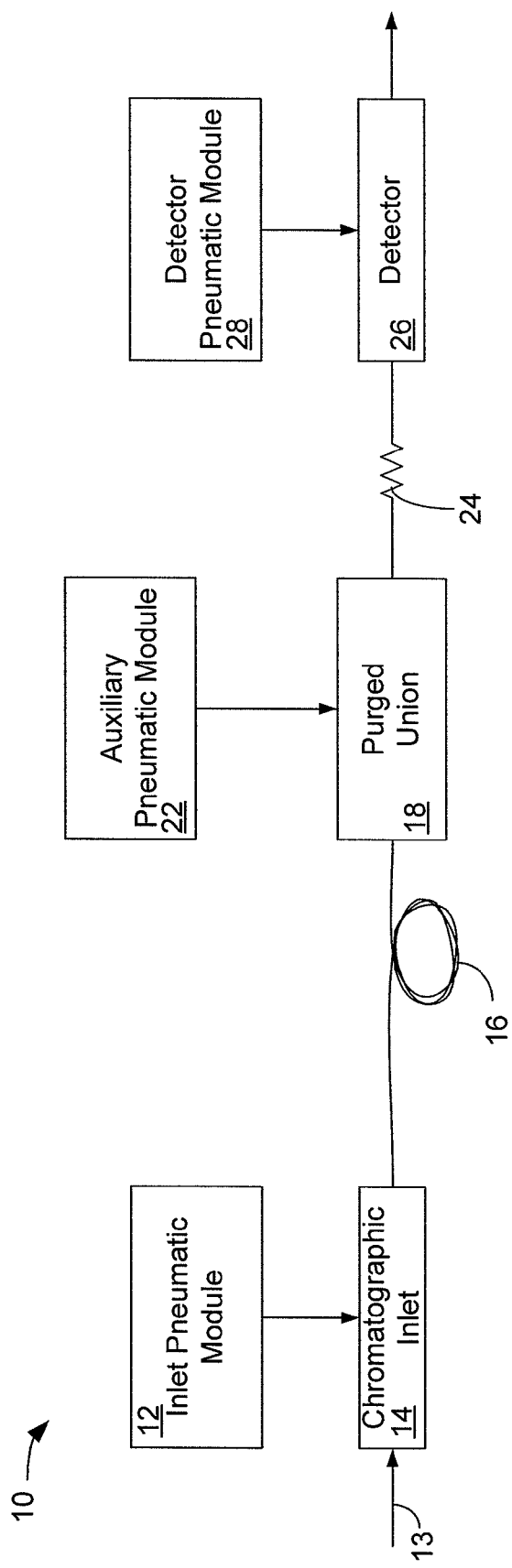
FIG. 1 is a schematic diagram illustrating an arrangement for column backflush in an existing gas chromatograph.
Figure 2:
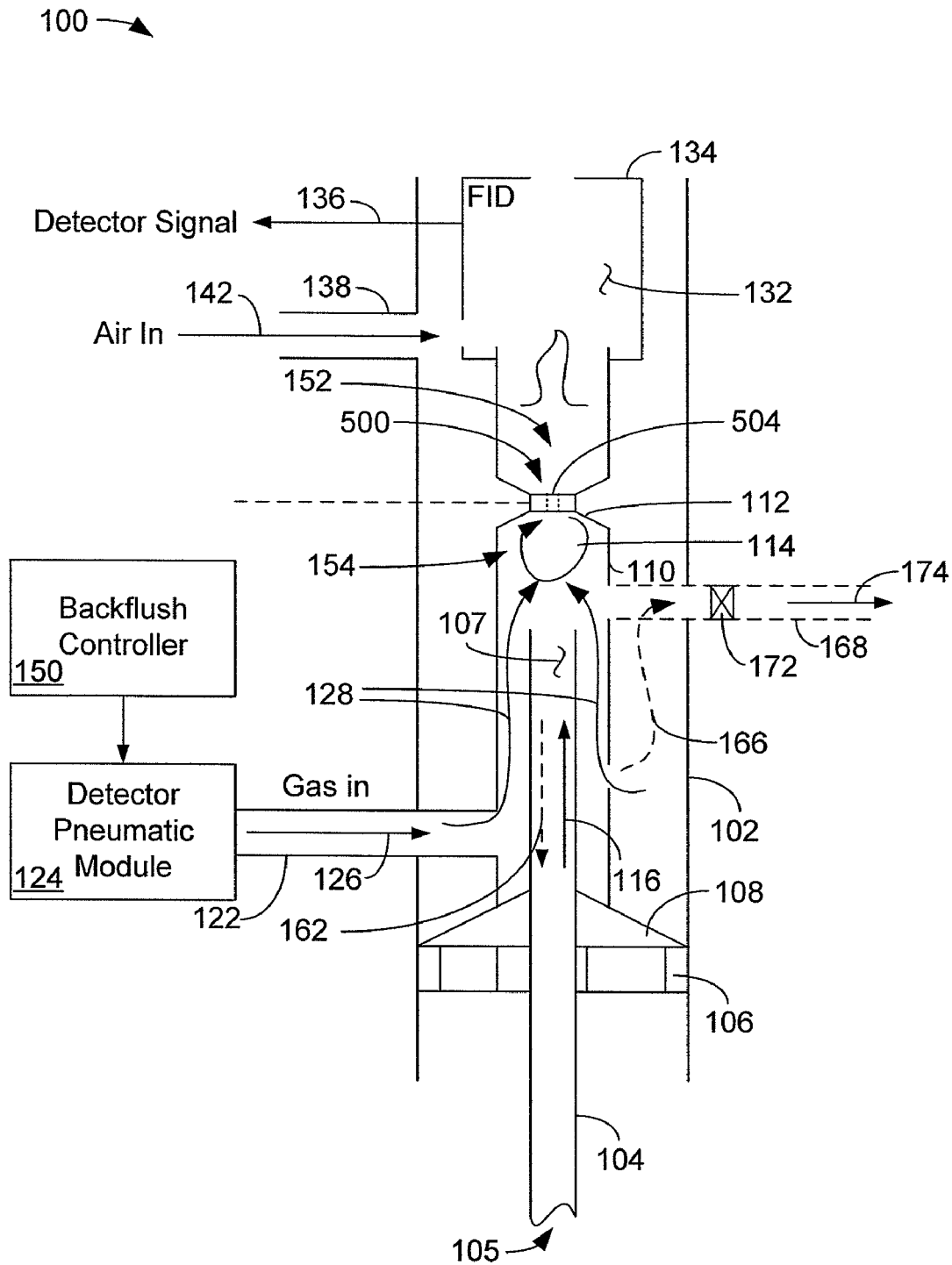
FIG. 2 is a schematic diagram illustrating a gas chromatograph detector system with integrated backflush capability in accordance with an embodiment of the invention.

FIG. 2 is a schematic diagram illustrating a gas chromatograph detector system 100 with integrated backflush capability in accordance with an embodiment of the invention. The gas chromatograph detector system 100 with integrated backflush capability illustrates a portion of a gas chromatograph system. Those skilled in the art will understand that a gas chromatograph system includes additional components, which are not shown here for simplicity.

The gas chromatograph detector system 100 with integrated backflush capability includes a detector inlet 102 that is designed to receive a chromatographic column, also referred to as a column, 104. The column 104 can be a packed column, a capillary column, or any other chromatographic column as known to those skilled in the art. The column 104 can be coupled to the detector inlet 102 in a variety of ways. In an embodiment, the column 104 is coupled to the detector inlet 102 using a backing nut 106 and a ferrule 108 to fluidically couple and seal the column 104 to the detector inlet 102.

The column 104 includes a column entrance 105 and a column exit 107. Typically, a chromatographic column can be many meters in length, depending on the type of material sought to be analyzed. During normal chromatographic operation, a material under test travels from the column entrance 105 toward the column exit 107. The material under test emerges from the column exit 107 and is referred to as the elutant, and is indicated using the arrow 116. In the example described in FIG. 2, the detector 134 can be a flame ionization detector (FID). However, as will be described below, other detectors can be implemented.

In this example, the column 104 is inserted into a jet 110. The jet 110 includes a column stop 112 against which the column 104 is pressed and then relieved, such that the column exit 107 is spaced apart from the column stop 112, thus creating a mixing region 114. This practice is a typical column installation procedure for many current capillary gas chromatograph detectors. In an embodiment, a detector pneumatic module 124 controls normal chromatographic pressures and flows and, in an embodiment, controls the flow of gas through port 122, which allows an increased flow of gas to flow into the detector inlet 102, with a resultant increase in pressure. The increased flow of gas is illustrated using arrow 126. The detector pneumatic module 124 is coupled to one or more gas sources (not shown), and provides one or more pressure regulated gasses and constitutes a pressure regulated gas source. In an embodiment, the increased flow and pressure of gas is used to backflush the column 104 under the control of a backflush controller 150. The operation of the backflush controller 150 will be described below. For example, in the case of a flame ionization detector, the gas might be, for example, hydrogen ($H_2$), which mixes with the elutant 116 from the column 104 in the mixing region 114 before it passes into the detection zone 132 of the detector 134. The $H_2$ serves as the combustion fuel for the flame ionization detector 134. In the case of a flame ionization detector, combustion air 142 is also provided via port 138.

In accordance with an embodiment of the gas chromatograph detector system 100 with integrated backflush capability, the jet 110 includes an integrated restriction element 500. The integrated restriction element 500 can be an additional part that is added to, inserted within, or otherwise associated with the detector 134. Alternatively, the integrated restriction element 500 can be formed by modifying an existing structure within the detector 134. Alternative embodiments of an integrated restriction element 500 will be described below. In an embodiment, the integrated restriction element 500 comprises an orifice 504. However, as will be described below, other restriction elements having different structures are possible, as are alternative restriction element locations within the detector 134.

When the pressure at the column exit 107 exceeds the pressure at the column entrance 105, fluid flow reverses (i.e., backflushes) though the column 104. The orifice 504 allows a high pressure region 154 to be created between the restriction element 500 and the column exit 107 by restricting the flow of gas into the detector region 132. As an example, the detector pneumatic module 124, under the control of the backflush controller 150, is used to adjust, control, or otherwise change the pressure at the column exit 107 relative to the pressure at the column entrance 105. The detector pneumatic module 124 can be controlled to create a higher relative pressure at the column exit 107 than at the column entrance 105 thus causing a backflush flow in the column 104, indicated using arrow 162, to backflush the column 104. By resisting gas flow, the orifice 504 in the restriction element 500 allows the creation of a high pressure region 154. If the pressure in the region 154 between the column exit 107 and the integrated restriction element 500 is higher than the pressure at the column entrance 105, flow through the column 104 is reversed, thus causing a backflush flow in the column 104, indicated using arrow 162, to backflush the column 104. The integrated restriction element 500 also creates an elevated pressure, sometimes referred to as a backpressure, during analysis. The pressure drop across the integrated restriction element 500 is caused by the flow of the column elutant and any additional gas. Precise control of this backpressure is important for highest precision of analyte retention times (a key metric in gas chromatography) since the elutant retention time is related to flow rate through the column, which is in turn related to the pressure differential between column entrance 105 and column exit 107. Most gas chromatograph detectors operate at atmospheric pressure (1 atm, 14.7 psia). With the integrated restriction described herein, the elevated pressure at the column exit 107 during analysis is typically small (e.g. 4 psig, 18.7 psia) but must exist to force gas and elutant to flow into the detection region 132 and must be measured and controlled precisely.

The pressure differential between the column exit 107 and the column entrance 105 to create a backflush flow can be created by increasing the pressure at the column exit 107 such that it exceeds the pressure at the column entrance 105, by lowering the pressure at the column entrance 105 such that it is less than the pressure at the column exit 107 or by a combination of both. The larger the pressure differential between the column exit 107 and the column entrance 105, the higher the backflush flow rate. As used herein, a positive pressure differential refers to a condition in which the pressure at the column entrance 105 is higher than a pressure at the column exit 107; and a negative pressure differential refers to a condition in which a pressure at the column entrance 105 is lower than a pressure at the column exit 107. A negative pressure differential exists during backflush.

In an embodiment, the orifice 504 provides a restriction integrated into the jet 110, so that the detector pneumatic module 124 used to supply $H_2$ fuel gas for normal detector operation can also be controlled to increase the pressure at the column exit 107 above the pressure at the column inlet 105 to backflush the column 104.

As used herein, the terms "low pressure" and "high pressure" are intended to be relative to each other. The region 152 is typically at atmospheric pressure, and the region 154 is typically at least slightly elevated with respect to region 152. Further, the region 152 may also normally operate under a vacuum such as in the case of a mass spectrometer (MS) detector.

During normal chromatographic/detector operation, the flow of gas 126 combines with the elutant 116 as indicated using arrow 128 in the mixing region 114, creates a known elevated pressure as it passes through the orifice 504 to the atmospheric pressure region 152, and enters the detection zone 132. At the same time, the pressure at the column entrance 105 is higher than the pressure at the column exit 107, thereby creating forward flow through the column 104. In the detection zone 132, the flame ionization detector operation burns the fuel gas and elutant and detects the combustion products of the elutant 116 through the detection zone. The detector signal 136 is filtered, amplified, digitized or otherwise processed and recorded in ways known to those skilled in the art.

However, when it is desirable to backflush the column 104, the pressure at the column exit 107 is raised above the pressure at the column entrance 105. This is accomplished by increasing the pressure at the column exit 107, decreasing the pressure at the column entrance 105, or by a combination of both. To increase the pressure at the column exit 107, the flow rate of the gas 126 is increased. The integrated restriction element 500 resists the additional flow, creating a higher backpressure at the column exit 107 side of the integrated restriction 500. Column inlet pressure at the column entrance 105 can be reduced using an inlet pressure control device (not shown in FIG. 2), which can be implemented as part of an inlet pneumatic module.

The integrated restriction element 500 is integrated into the detector in such a way that the user of the system does not have to change their work habits (i.e., column installation process is the same as if the restrictor were not present). Further, the integrated restriction element 500 is integrated in such a way that it allows existing detector gas supply and existing gas control that is normally used for performing analysis to also be used to create the backflush flow, without additional components and without any system reconfiguration, other than changing the gas flow, which is facilitated by standard detector electronic pressure controllers under the control of the backflush controller 150.

In the case of an FID, as described above, the jet is replaceable. Therefore, converting an existing non-backflushing FID into one that can backflush as described herein requires only exchanging the existing jet for a jet having an integrated restriction, as described herein, and updating any operating software or firmware to allow operation using the new jet.

Also shown in FIG. 2 is an optional port 168. The port 168 can be included as part of the gas chromatograph detector system 100 with integrated backflush capability and used in what is referred to as a "solvent dump" mode. The term "solvent dump" refers to the ability to cause the elutant to bypass the detector. For example, there may be instances in which it is desirable to have the ability to cause the elutant to bypass the detector because the sample solvent or one or more of the sample components eluting from the column may damage the detector with prolonged exposure. In such a mode, an optional valve 172 can be opened, thus causing the flow of gas 126 to carry the elutant along the path indicated by the arrow 166 and through the port 168, as indicated using arrow 174. If the valve 172 and the port 168 are included, then during normal operation, a small trickle flow of gas 126 can be used to keep the system contaminant free. Then, if desired, the valve 172 can be opened to allow the gas 126 to carry the majority of elutant along the path indicated by the arrow 166 and through the port 168, as indicated using arrow 174, thereby greatly reducing or eliminating the amount of elutant reaching the detector zone. Although not shown in the alternative embodiments for simplicity, this "solvent dump" capability can be included on all embodiments described herein.

Figure 3:
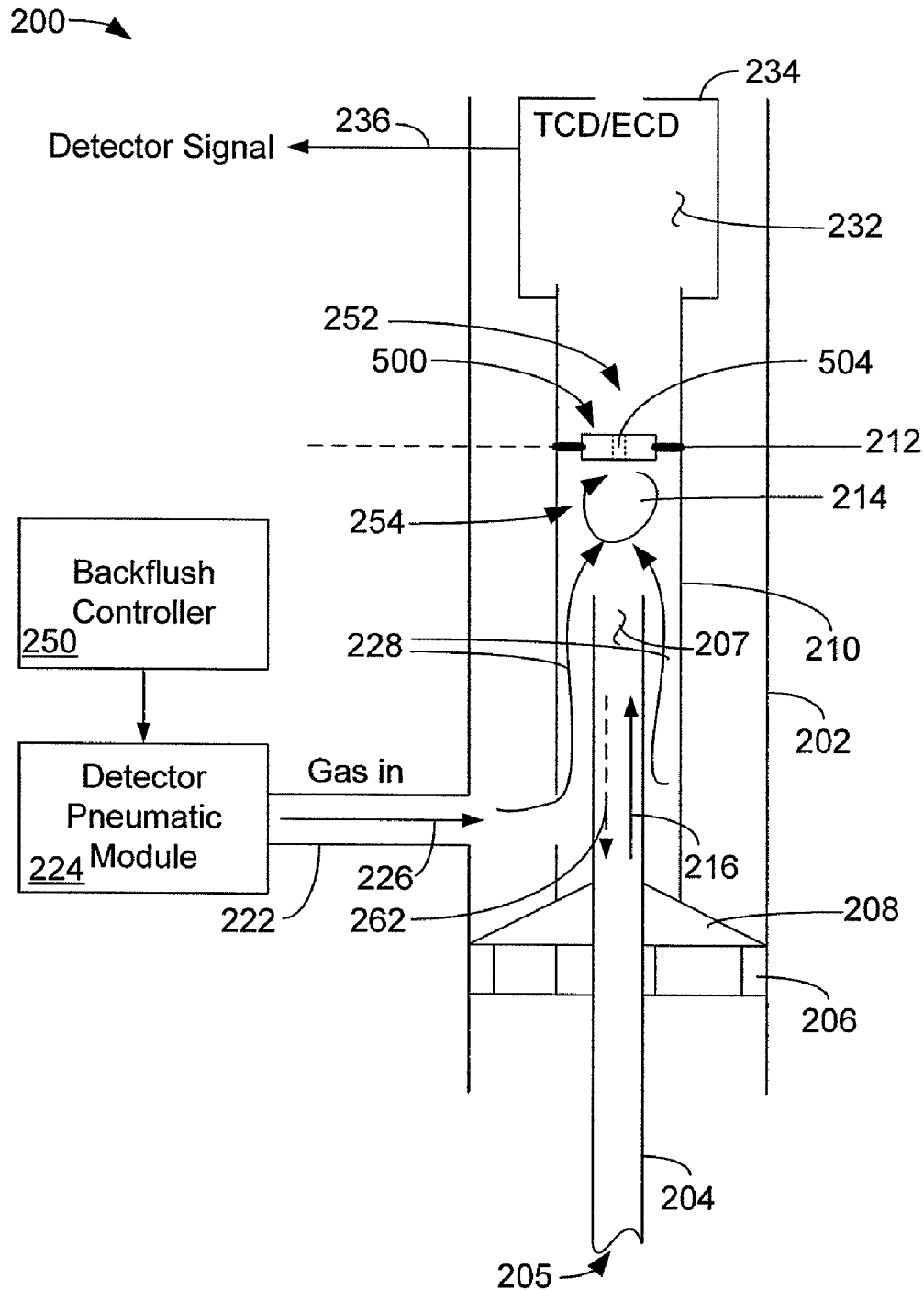
FIG. 3 is a schematic diagram illustrating a gas chromatograph detector system with integrated backflush capability in accordance with an alternative embodiment of the invention.

FIG. 3 is a schematic diagram illustrating a gas chromatograph detector system 200 with integrated backflush capability in accordance with an alternative embodiment of the invention. The gas chromatograph detector system 200 with integrated backflush capability illustrates a portion of a gas chromatograph system. Those skilled in the art will understand that a gas chromatograph system includes additional components, which are not shown here for simplicity.

The gas chromatograph detector system 200 with integrated backflush capability includes a detector inlet 202 that is designed to receive a chromatographic column, also referred to as a column, 204. The column 204 can be a packed column, a capillary column, or any other chromatographic column as known to those skilled in the art. The column 204 can be coupled to the detector inlet 202 in a variety of ways. In an embodiment, the column 204 is coupled to the detector inlet 202 using a backing nut 206 and a ferrule 208 to fluidically couple and seal the column 204 to the detector inlet 202.

The column 204 includes a column entrance 205 and a column exit 207. Typically, a chromatographic column can be many meters in length, depending on the type of material sought to be analyzed. During normal chromatographic operation, a material under test travels from the column entrance 205 toward the column exit 207. The material under test emerges from the column exit 207 and is referred to as the eluant, and is indicated using the arrow 216. In the example described in FIG. 3, the detector 234 can be a thermal conductivity detector (TCD), or an electron capture detector (ECD). However, as will be described below, other detectors can be implemented.

In this example, the column 204 is inserted into a guide tube 210. The guide tube 210 includes a column stop 212 against which the column 204 is pressed and then relieved, such that the column exit 207 is spaced apart from the column stop 212, thus creating a mixing region 214. In an embodiment, a detector pneumatic module 224 controls normal chromatographic pressures and flows and, in an embodiment, controls an increased flow of gas through port 222, which allows the increased flow of gas to flow into the detector inlet 202. The increased flow of gas is illustrated using arrow 226. The detector pneumatic module 224 is coupled to one or more gas sources (not shown), and provides one or more pressure regulated gasses and constitutes a pressure regulated gas source. In an embodiment, the increased flow of gas and resultant increase in pressure is used to backflush the column 204 under the control of a backflush controller 250. The operation of the backflush controller 250 will be described below. For example, in the case of an electron capture detector, the increased flow of gas might be nitrogen ($N_2$), which mixes with the elutant 216 from the column 204 in the mixing region 214 before it passes into the detection zone 232 of the detector 234. The $N_2$ can help maintain chromatographic peak fidelity or could take an active role in the detection process. For example, with an ECD with radioactive sources, $N_2$ gas provides a background current from thermal electrons that is then reduced when elutants pass through the detection zone 232.

In accordance with an embodiment of the gas chromatograph detector system 200 with integrated backflush capability, the guide tube 210 includes an integrated restriction element 500. In an embodiment, the integrated restriction element 500 comprises an orifice 504. However, as will be described below, other restriction elements having different structures are possible. When the pressure at the column exit 207 exceeds the pressure at the column entrance 205, flow reverses (i.e., backflushes) though the column 204. The orifice 504 causes an elevated pressure in region 254 between the column exit 207 and the integrated restriction element 500 to be created between the restriction element 500 and the column exit 207 by restricting the flow of gas into the detector region 232. As an example, the detector pneumatic module 224, under the control of the backflush controller 250, is used to adjust, control, or otherwise change the pressure at the column exit 207 relative to the pressure at the column entrance 205. The detector pneumatic module 224 can be controlled to create a higher relative pressure at the column exit 207 than at the column entrance 205 thus causing a backflush flow in the column 204, indicated using arrow 262, to backflush the column 204. This backflush flow is accomplished by increasing the pressure at the column exit 207 to a level above the pressure at the column entrance 205. This pressure differential between the column exit 207 and the column entrance 205 can be created by increasing the pressure at the column exit 207 relative to the pressure at the column entrance 205, by lowering the pressure at the column entrance 205 relative to the pressure at the column exit 207, or by a combination of both. In an embodiment, the orifice 504 provides a restriction integrated into the guide tube 210, so that the detector pneumatic module 224 used for normal detector operation can also be used to increase the pressure at the column exit 207 above the pressure at the column exit 205 to backflush the column 204.

During normal chromatographic/detector operation, the flow of gas 226 combines with the elutant 216 as indicated using arrow 228 in the mixing region 214, creates a known elevated pressure as it passes through the orifice 504 to the atmospheric pressure region 252, and enters the detection zone 232. At the same time, the pressure at the column entrance 205 is higher than the pressure at the column exit 207, thereby creating forward flow through the column 204. In the detection zone 232, the thermal conductivity detector or the electron capture detector operation measures properties of the elutant and detects the elutant 216. The detector signal 236 is filtered, amplified, digitized or otherwise processed and recorded in ways known to those skilled in the art.

However, when it is desirable to backflush the column 204, the pressure at the column exit 207 is raised with respect to the pressure at the column entrance 205. This is accomplished by increasing the pressure at the column exit 207, decreasing the pressure at the column entrance 205, or a combination of both. To increase the pressure at the column exit 207, the flow rate of the gas 226 is increased. The integrated restriction element 500 resists the additional flow, creating a higher backpressure at the column exit 207 side of the integrated restriction element 500. Column inlet pressure at the column entrance 205 can be reduced using an inlet pneumatic module (not shown in FIG. 3).

The integrated restriction element 500 is integrated into the detector in such a way that the user of the system does not have to change their work habits (i.e., column installation process is the same as if the restrictor were not present). Further, the integrated restriction element 500 is integrated in such a way that it allows existing detector gas supply and existing gas control that is normally used for performing analysis to also be used to create the backflush flow, without additional components and without any system reconfiguration, other than changing the gas flow, which is facilitated by standard detector electronic pressure controllers under the control of the backflush controller 250.

In another example, the restriction can be integrated into a transfer line of a mass spectrometer (not shown). The mass spectrometer is generally operated under vacuum (e.g., $10^{-5}$ torr). With reference to FIG. 3, the TCD/ECD detector 234 would be a mass spectrometer, and the region 252 would normally operate under a vacuum. The remaining description of the embodiment shown in FIG. 3 would apply to the mass spectrometer detector; however, the integrated restriction would be more restrictive due to the larger pressure drop from column outlet to detector.

Figure 4:
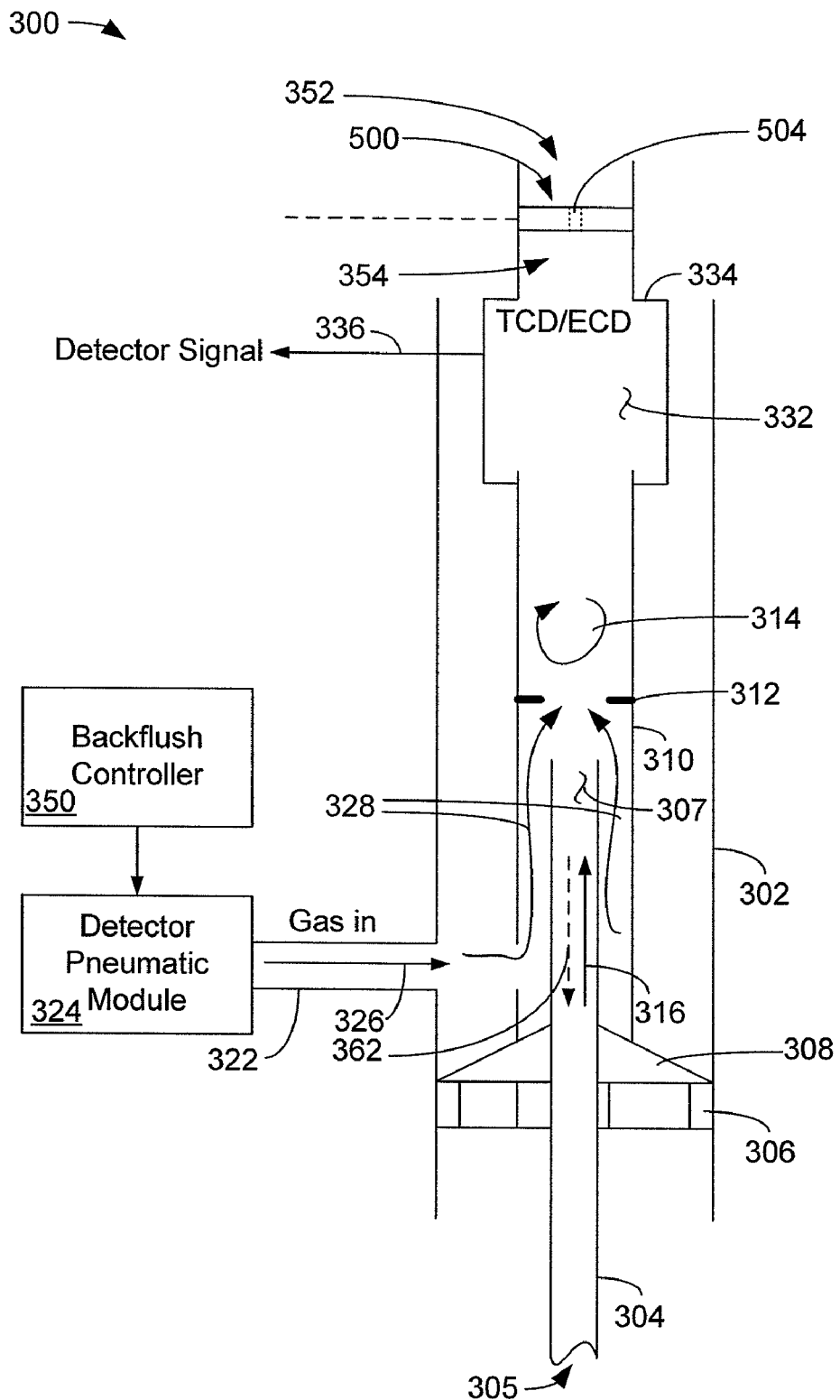
FIG. 4 is a schematic diagram illustrating a gas chromatograph detector system with integrated backflush capability in accordance with another alternative embodiment of the invention.

FIG. 4 is a schematic diagram illustrating a gas chromatograph detector system 300 with integrated backflush capability in accordance with another alternative embodiment of the invention. The gas chromatograph detector system 300 with integrated backflush capability is similar to the gas chromatograph detector system 200 with integrated backflush capability shown in FIG. 3, with the exception of the location of the integrated restriction element 500. With the integrated restriction element 500 located at the outlet of the detector as shown in FIG. 4, detection of elutants occurs at elevated pressures. This is a favorable condition for some gas chromatograph detectors such as a TCD. For other detectors, like an FID, detection is preferable at atmospheric pressure as described above. As mentioned above with regard to FIG. 2 and FIG. 3, the gas chromatograph detector system 300 with integrated backflush capability illustrates a portion of a gas chromatograph system. Those skilled in the art will understand that a gas chromatograph system includes additional components, which are not shown here for simplicity.

The gas chromatograph detector system 300 with integrated backflush capability includes a detector inlet 302 that is designed to receive a chromatographic column, also referred to as a column, 304 in a manner similar to that described above in FIG. 3. The column 304 can be coupled to the detector inlet 302 in variety of ways. In an embodiment, the column 304 is coupled to the detector inlet 302 using a backing nut 306 and a ferrule 308 to fluidically couple and seal the column 304 to the detector inlet 302. The column 304 includes a column entrance 305 and a column exit 307. Typically, a chromatographic column can be many meters in length, depending on the type of material sought to be analyzed. During normal chromatographic operation, a material under test travels from the column entrance 305 toward the column exit 307. The material under test emerges from the column exit 307 and is referred to as the elutant, and is indicated using the arrow 316. In the example described in FIG. 4, the detector 334 can be a thermal conductivity detector (TCD), or an electron capture detector (ECD), as described above.

In this example, the column 304 is inserted into a guide tube 310. The guide tube 310 includes a column stop 312 against which the column 304 is pressed and then relieved, such that the column exit 307 is spaced apart from the column stop 312, thus creating a mixing region 314. In an embodiment, a detector pneumatic module 324 controls normal chromatographic pressures and flows and, in an embodiment, controls an increased flow of gas through port 322, which allows the increased flow of gas to flow into the detector inlet 302. The increased flow of gas is illustrated using arrow 326. The detector pneumatic module 324 is coupled to one or more gas sources (not shown), and provides one or more pressure regulated gasses and constitutes a pressure regulated gas source. In an embodiment, the increased flow and resultant pressure of gas is used to backflush the column 304 under the control of a backflush controller 350. The operation of the backflush controller 350 will be described below. For example, in the case of an electron capture detector, the increased flow of gas might be, for example, nitrogen ($N_2$), which mixes with the elutant 316 from the column 304 in the mixing region 314 before it passes into the detection zone 332 of the detector 334.

In accordance with an embodiment of the gas chromatograph detector system 300 with integrated backflush capability, the integrated restriction element 500 comprising the orifice 504 is integrated within the detector 334. When the pressure at the column exit 307 exceeds the pressure at the column entrance 305, flow reverses (i.e., backflushes) though the column 304. The orifice 304 causes an elevated pressure in region 354 to be created between the integrated restriction element 500 and the column exit 307 by restricting the flow of gas out of the detector region 332. As an example, the detector pneumatic module 324, under the control of the backflush controller 350, is used to adjust, control, or otherwise change the pressure at the column exit 307 relative to the pressure at the column entrance 305, to create a higher relative pressure at the column exit 307 than at the column entrance 305. This pressure differential causes a backflush flow in the column 304, indicated using arrow 362, to backflush the column 304, as described above. This backflush flow is accomplished by increasing the pressure at the column exit 307 to a level above the pressure at the column entrance 305. This pressure differential between the column exit 307 and the column entrance 305 can be created by increasing the pressure at the column exit 307 relative to the pressure at the column entrance 305, by lowering the pressure at the column entrance 305 relative to the pressure at the column exit 307, or by a combination of both. In an embodiment, the orifice 504 provides a restriction integrated into the detector 334, so that the detector pneumatic module 324 can be controlled to increase the pressure at the column exit 307 above the pressure at the column exit 305 to backflush the column 304.

During normal chromatographic/detector operation, the flow of gas 326 combines with the elutant 316 as indicated using arrow 328 in the mixing region 314, creates a known elevated pressure in region 352, and enters into the detection zone 332. At the same time, the pressure at the column entrance 305 is higher than the pressure at the column exit 307, thereby creating forward flow through the column 304. In the detection zone 332, the thermal conductivity detector or the electron capture detector operation measures properties of the elutant and detects the elutant 316. The detector signal 336 is filtered, amplified, digitized or otherwise processed and recorded in ways known to those skilled in the art.

However, when it is desirable to backflush the column 304, the pressure at the column exit 307 is raised with respect to the pressure at the column entrance 305. This is accomplished by increasing the pressure at the column exit 307, decreasing the pressure at the column entrance 305, or a combination of both. To increase the pressure at the column exit 307, the flow rate of the additional gas 326 is increased. The integrated restriction 500 resists the additional flow, creating a higher backpressure at the column exit 307 side of the integrated restriction element 500. Column inlet pressure at the column entrance 305 can be reduced using an inlet pneumatic module (not shown in FIG. 4).

The integrated restriction element 500 is integrated into the detector in such a way that the user of the system does not have to change their work habits (i.e., column installation process is the same as if the restrictor were not present). Further, the integrated restriction element 500 is integrated in such a way that it allows existing detector gas supply and existing gas control that is normally used for performing analysis to also be used to create the backflush flow, without additional components and without any system reconfiguration, other than changing the gas flow, which is facilitated by standard detector electronic pressure controllers.

Figure 5:
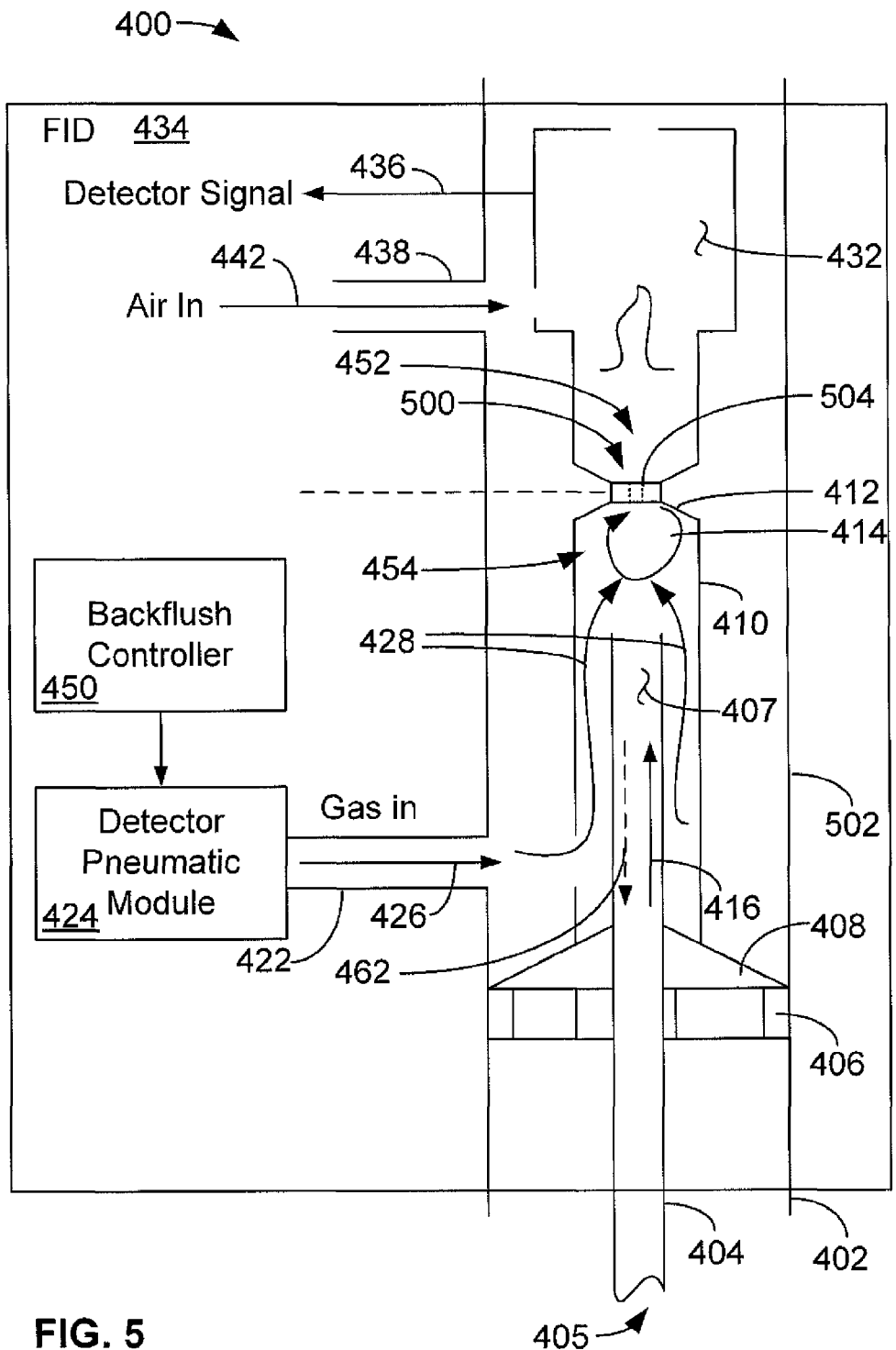
FIG. 5 is a schematic diagram illustrating a gas chromatograph detector system with integrated backflush capability in accordance with another alternative embodiment of the invention.

FIG. 5 is a schematic diagram illustrating a gas chromatograph detector system 400 with integrated backflush capability in accordance with another alternative embodiment of the invention. The gas chromatograph detector system 400 with integrated backflush capability is similar to the gas chromatograph detector system 100 with the exception that the detector system 400 is included within a detector. In this example, the detector is a flame ionization detector 434, but other detectors are possible. The gas chromatograph detector system 400 with integrated backflush capability illustrates a portion of a gas chromatograph system. Those skilled in the art will understand that a gas chromatograph system includes additional components, which are not shown here for simplicity.

The gas chromatograph detector system 400 with integrated backflush capability includes a detector inlet 402 that is designed to receive a chromatographic column, also referred to as a column, 404, as described above. The column 404 can be coupled to the detector inlet 402 in variety of ways. In an embodiment, the column 404 is coupled to the detector inlet 402 using a backing nut 406 and a ferrule 408 to fluidically couple and seal the column 404 to the detector inlet 402. The column 404 can be a packed column, a capillary column, or any other chromatographic column as known to those skilled in the art.

The column 404 includes a column entrance 405 and a column exit 407. Typically, a chromatographic column can be many meters in length, depending on the type of material sought to be analyzed. During normal chromatographic operation, a material under test travels from the column entrance 405 toward the column exit 407. The material under test emerges from the column exit 407 and is referred to as the elutant, and is indicated using the arrow 416. In the example described in FIG. 5, the detector 434 is a flame ionization detector (FID). However, other detectors can be implemented.

In this example, the column 404 is inserted into a jet 410. The jet 410 includes a column stop 412 against which the column 404 is pressed and then relieved, such that the column exit 407 is spaced apart from the column stop 412, thus creating a mixing region 414. In an embodiment, a detector pneumatic module 424 controls normal chromatographic pressures and flows and, in an embodiment, controls the flow of gas through port 422, which allows an increased flow of gas to flow into the detector inlet 402 with a resultant increase in pressure. The increased flow of gas is illustrated using arrow 426. The detector pneumatic module 424 is coupled to one or more gas sources (not shown), and provides one or more pressure regulated gasses and constitutes a pressure regulated gas source. In an embodiment, the increased flow and pressure of gas is used to backflush the column 404 under the control of a backflush controller 450. The operation of the backflush controller 450 will be described below. For example, in the case of a flame ionization detector, the gas might be, for example, hydrogen (H$_2$), which mixes with the elutant 416 from the column 404 in the mixing region 414 before it passes into the detection zone 432. The H$_2$ serves as a combustion fuel for the flame ionization detector 434. In the case of a flame ionization detector, combustion air 442 is also provided via port 438.

In accordance with an embodiment of the gas chromatograph detector system 400 with integrated backflush capability, the jet 410 includes an integrated restriction element 500. The integrated restriction element 500 comprises an orifice 504. However, as will be described below, other restriction elements having different structures are possible. When the pressure at the column exit 407 exceeds the pressure at the column entrance 405, flow reverses (i.e., backflushes) though the column 404. The orifice 504 allows an elevated pressure in region 454 to be created between the restriction structure 502 and the column exit 407. As an example, the detector pneumatic module 424, under the control of the backflush controller 450, is used to adjust, control, or otherwise change the pressure at the column exit 407 relative to the pressure at the column entrance 405, to create a higher relative pressure at the column exit 407 than at the column entrance 405. The detector pneumatic module 424 can be controlled to create a higher relative pressure at the column exit 407 than at the column entrance 405 thus causing a backflush flow in the column 404, indicated using arrow 462, to backflush the column 404. By resisting gas flow, the orifice 504 in the restriction element 500 allows the creation of a high pressure region 454 between the column exit 407 and the integrated restriction element 500. If the pressure in the region 454 is higher than the pressure at the column entrance 405, flow through the column 404 is reversed, thus causing a backflush flow in the column 404, indicated using arrows 462, to backflush the column 404.

During normal chromatographic/detector operation, the gas 426 combines with the elutant 416 as indicated using arrow 428 in the mixing region 414, creates a known elevated pressure as it passes through the orifice 504 to the atmospheric pressure region 452, and enters the detection zone 432. At the same time, the pressure at the column entrance 405 is higher than the pressure at the column exit 407, thereby creating forward flow through the column 404. In the detection zone 432, the flame ionization detector operation burns the fuel gas and elutant and detects the combustion products of the elutant 416 through the detection zone. The detector signal 436 is filtered, amplified, digitized or otherwise processed and recorded in ways known to those skilled in the art.

However, when it is desirable to backflush the column 404, the pressure at the column exit 407 is raised above the pressure at the column entrance 405. This is accomplished by increasing the pressure at the column exit 407, decreasing the pressure at the column entrance 405, or a combination of both. To increase the pressure at the column exit 407, the flow rate of the gas 426 is increased. The integrated restriction element 500 resists the additional flow, creating a higher backpressure at the column exit 407 side of the integrated restriction element 500. Column inlet pressure at the column entrance 405 can be reduced using an inlet pneumatic module (not shown in FIG. 5).

The integrated restriction element 500 is integrated into the detector in such a way that the user of the system does not have to change their work habits (i.e., column installation process is the same as if the restrictor were not present). Further, the integrated restriction element 500 is integrated in such a way that it allows existing detector gas supply and existing gas control that is normally used for performing analysis to also be used to create the backflush flow, without additional components and without any system reconfiguration, other than changing the gas flow, which is facilitated by standard detector electronic pressure controllers under the control of the backflush controller 150.

FIGS. 6A through 11D illustrate various alternative embodiments of a restriction element that can be located within a detector. In some embodiments, the restriction element comprises a separate structure that includes a restriction, and that can be inserted within various components of a detector. In other embodiments, the restriction element is formed using an existing detector element or structure, without any additional parts or components.

FIGS. 6A and 6B are schematic diagrams illustrating an embodiment of an integrated restriction element. FIG. 6A is a cross-sectional view illustrating an embodiment of an integrated restriction element 500. The integrated restriction element 500 can be part of a detector, or can be a component added to a detector. In an embodiment, the integrated restriction element 500 includes a restriction structure 502 which includes an orifice 504. In an embodiment, the orifice 504 can be a machined hole, a laser ablated opening, or any other opening that forms a restriction. FIG. 6B is a plan view illustrating the restriction structure 502 and the orifice 504. In an embodiment, the restriction structure 502 can have a thickness of approximately 0.1-0.6 mm and the orifice 504 can have a diameter ranging between 5 and 70 micrometers (μm). However, other dimensions are possible.

FIGS. 7A and 7B are schematic diagrams illustrating an alternative embodiment of a restriction element. FIG. 7A is a cross-sectional view illustrating an alternative embodiment of an integrated restriction element 600. In this example, the integrated restriction element 600 can be a jet 610, or a portion of a jet, having a restriction 615. In this example, the restriction 615 is referred to as a linear restriction. FIG. 7B is a plan view illustrating the jet 610 and the linear restriction 615. In an embodiment, the restriction 615 can have a diameter of approximately 50-150 μm, and a length, l, for example, between 0.75 and 15 mm. However, other dimensions are possible.

FIGS. 8A and 8B are schematic diagrams illustrating another alternative embodiment of a restriction element. FIG. 8A is cross sectional view illustrating another alternative embodiment of an integrated restriction element 700. The integrated restriction element 700 includes a restriction structure 702 and a porous frit 704 that acts as the restriction. Alternatively, the porous frit 704 can be part of an existing structure within a detector. FIG. 8B is a plan view illustrating the restriction structure 702 and the porous frit 704. In an embodiment, the restriction structure 702 can have a thickness of approximately 1-10 mm and the porous frit 704 can have a diameter ranging between 0.5 and 3 mm. However, other dimensions are possible.

Figure 9:
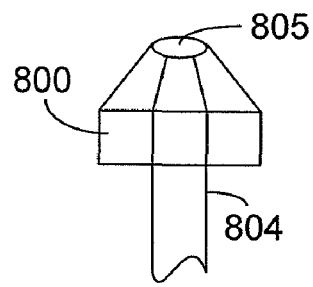
FIG. 9 is a schematic diagram illustrating another alternative embodiment of a restriction element.

FIG. 9 is a schematic diagram illustrating another alternative embodiment of a restriction element. The embodiment shown in FIG. 9 includes a jet 800. The jet 800 can be, for example, a jet for a flame ionization detector as described above. The jet 800 receives a column 804, as described above, and includes a restriction 805. The restriction 805 can be, for example, an orifice, a linear restriction, a porous frit, or any other restriction.

Figure 10A:
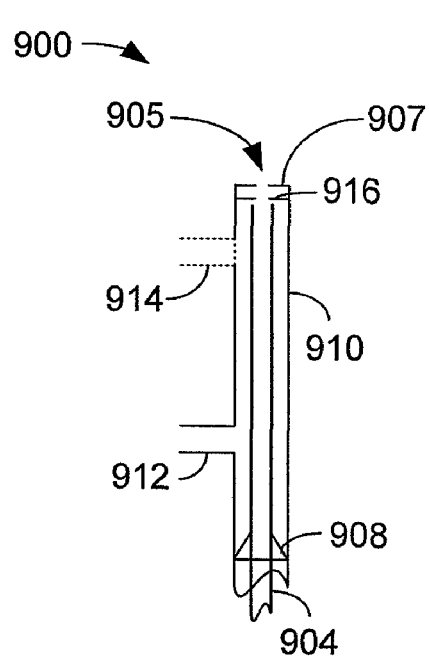
FIGS. 10A and 10B are schematic diagrams illustrating alternative embodiments of a restriction element.
Figure 10B:
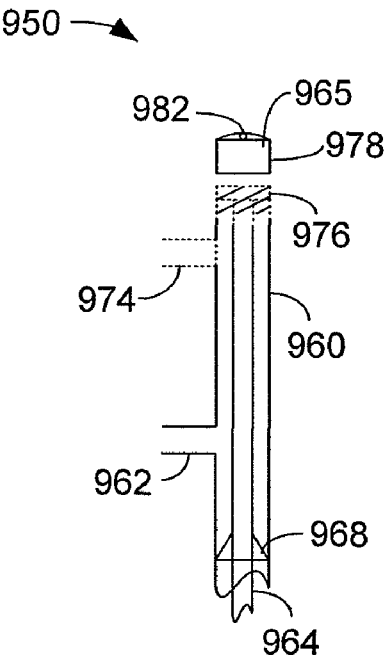

FIGS. 10A and 10B are schematic diagrams illustrating alternative embodiments of a restriction element.

FIG. 10A is a schematic diagram illustrating an alternative embodiment 900 of a restriction element within a transfer line of a mass spectrometer. The embodiment shown in FIG. 10A includes a mass spectrometer transfer line 910. The mass spectrometer transfer line 910 comprises an integrated restriction 905 at the end 907 of the transfer line 910 that enters a mass spectrometer (not shown). An analytical column 904 is inserted into an end of the mass spectrometer transfer line 910 against a column stop 916, is pressed and then relieved, such that the column exit is spaced apart from the column stop 916, thus creating a mixing region, as described above. The analytical column 904 is sealed to the transfer line 910 using seal 908. In this example, the integrated restriction 905 is an orifice that is created in the end 907 of the transfer line 910 by, for example, machining, laser ablation, or another technique. No additional parts or pieces are used to create the orifice 905. As in current practice, the seal 908 is created for the mass spectrometer transfer line 910 at the end opposite the integrated restriction 905, where the mass spectrometer transfer line 910, enters the gas chromatograph (not shown). A side port 912 supplies the additional gas between the orifice 905 and the column 904. An optional solvent dump port 914 can also be part of the transfer line 910, as discussed above.

FIG. 10B is a schematic diagram illustrating an alternative embodiment 950 of a restriction element within a transfer line of a mass spectrometer. The embodiment shown in FIG. 10B includes a mass spectrometer transfer line 960. In the embodiment shown in FIG. 10B, the mass spectrometer transfer line 960 comprises a removable integrated restriction element 965 comprising a removable cap 978 having an orifice 982. The removable cap 978 can be threaded onto a threaded end 976 of the transfer line 960. An analytical column 964 is inserted into an end of the mass spectrometer transfer line 960, as described above. The analytical column 964 is sealed to the transfer line 960 using seal 968. In this example, the removable integrated restriction element 965 includes an orifice 982 that is created in the removable cap 978 by, for example, machining, laser ablation, or another technique. As in current practice, the seal 968 is created for the mass spectrometer transfer line 960 at the end opposite the removable integrated restriction element 965, where the mass spectrometer transfer line 960, enters the gas chromatograph (not shown). A side port 962 supplies the additional gas between the orifice 982 and the column 964. An optional solvent dump port 974 can also be part of the transfer line 960, as discussed above.

Figure 11A:
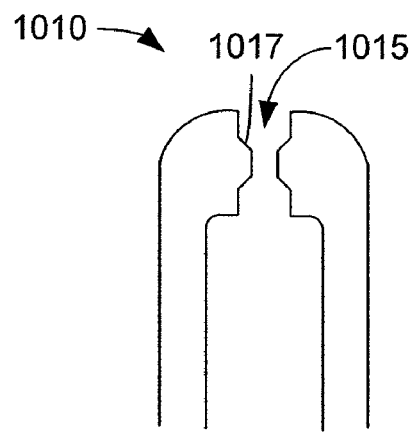
FIGS. 11A through 11D are schematic diagrams illustrating additional embodiments of a restriction element.

FIGS. 11A through 11D are schematic diagrams illustrating additional embodiments of a restriction element. FIG. 11A is a schematic diagram illustrating a jet 1010 of an FID having an integrated linear restriction element 1015. The integrated linear restriction element 1015 can contain, for example, a tapered feature 1017 in an end of the jet 1010.

Figure 11B:
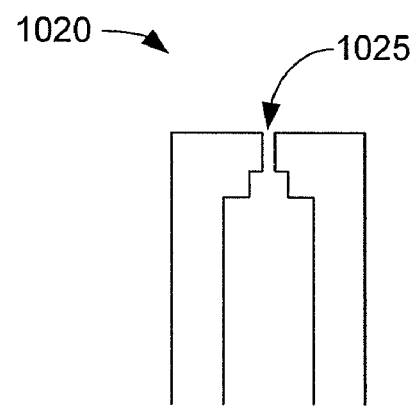

FIG. 11B is a schematic diagram illustrating a mass spectrometer transfer line 1020 having an integrated linear restriction element 1025. The integrated linear restriction element 1025 can be, for example, a linear opening in an end of the transfer line 1020.

Figure 11C:
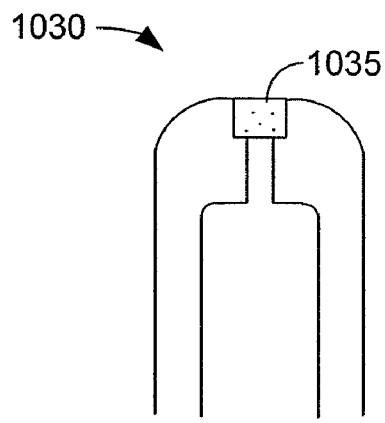

FIG. 11C is a schematic diagram illustrating a jet 1030 of an FID having an integrated restriction element 1035. The integrated restriction element 1035 can be, for example, a porous frit 1035 that can be press fit, or otherwise assembled, into an end of the jet 1030.

Figure 11D:
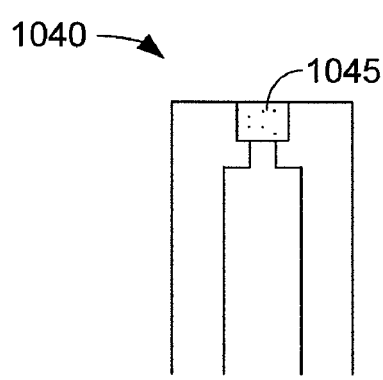

FIG. 11D is a schematic diagram illustrating a mass spectrometer transfer line 1040 having an integrated restriction element 1045. The integrated restriction element 1045 can be, for example, a porous frit 1045 that can be press fit, or otherwise assembled, into an end of the transfer line 1040.

Figure 12:
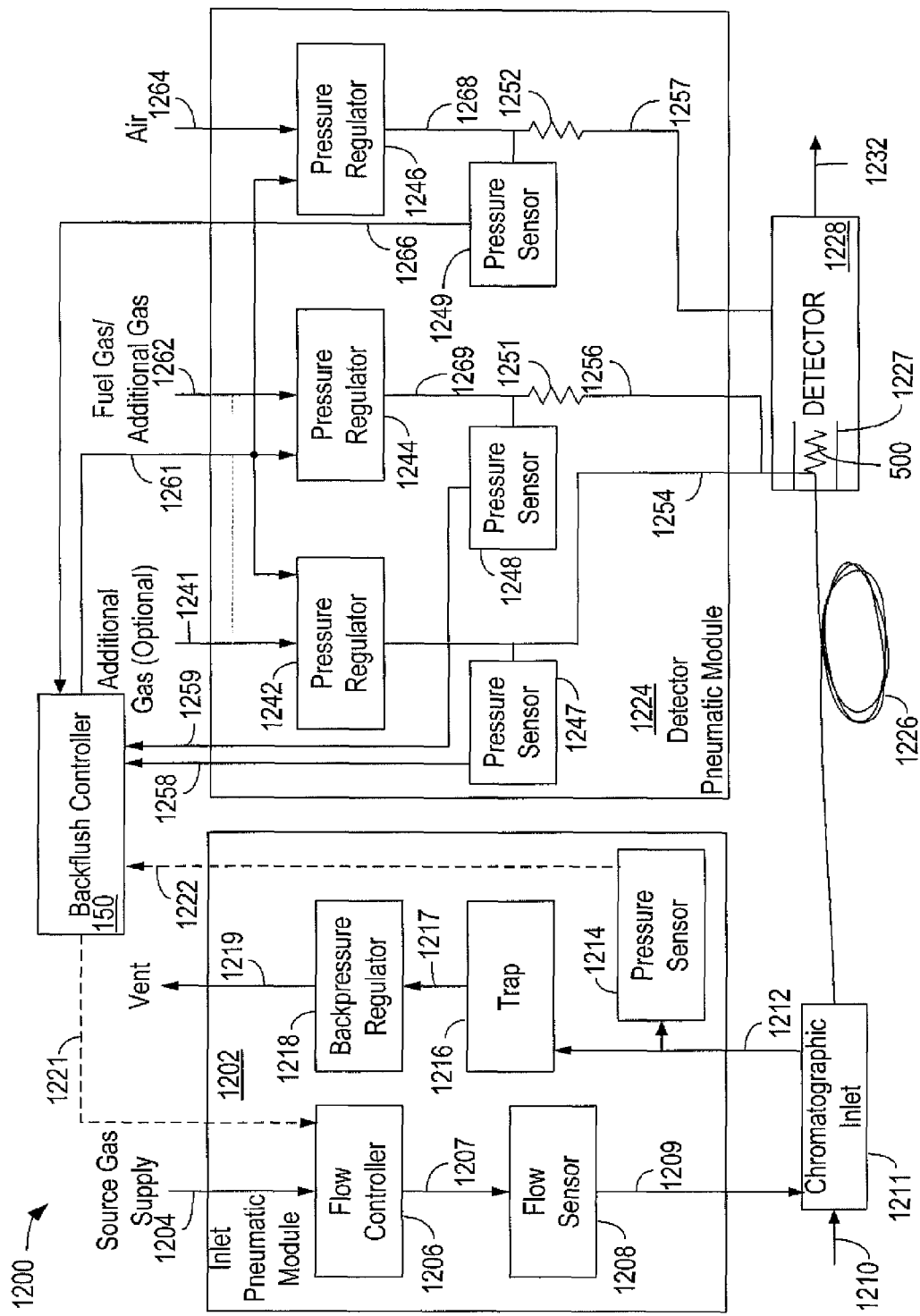
FIG. 12 is a block diagram illustrating a simplified gas chromatograph in which an embodiment of the integrated backflush system can be implemented.

FIG. 12 is a block diagram illustrating a simplified gas chromatograph 1200, in which an embodiment of the gas chromatograph detector system with integrated backflush capability can be implemented. The gas chromatograph 1200 is shown as being implemented using a flame ionization detector as the detector engine. However, any of the embodiments of the gas chromatograph integrated backflush system described herein can be implemented in the system 1200.

The gas chromatograph 1200 includes an inlet pneumatic module 1202 coupled to a chromatographic inlet 1211. The inlet pneumatic module 1202 receives a source gas supply over connection 1204, which is provided to a flow controller 1206 to the chromatographic inlet 1211. As an example, the source gas supply received over connection 1204 can be a flow of a carrier gas, into which a sample is introduced over connection 1210 to the chromatographic inlet, as known in the art. The flow controller 1206 sets the total flow of carrier gas over connection 1207 through a flow sensor 1208. The flow sensor 1208 measures the total flow of the carrier gas flowing through connection 1209 to the chromatographic inlet 1211.

The chromatographic inlet 1211 is also connected via connection 1212 to a pressure sensor 1214 and to a trap 1216. The trap 1216 accepts a purge flow of gas during normal operation as well as the material that is backflushed out of the chromatographic column 1226 during backflush, and is a typical component of a split/splitless inlet, as known to those skilled in the art. The pressure sensor 1214 determines the pressure at the inlet of the column 1226. The trap 1216 is connected over connection 1217 to a backpressure regulator 1218, which is vented over connection 1219.

A chromatographic column 1226 is connected to the chromatographic inlet 1211. To effectively separate compounds of interest during chromatography, the analytical column 1226 may be heated to temperatures well above ambient temperature. The temperature to which the analytical column 1226 is heated is dependent on the type of sample being analyzed and may vary during a sample run to analyze multiple compounds covering a wide volatility range (related to retention) from a single sample. Accordingly, the analytical column 1226 may be located in a temperature chamber, also referred to as an oven, which is not shown here for simplicity.

The exit of the chromatographic column 1226 is coupled to a detector inlet 1227, which is part of the detector 1228. In accordance with an embodiment, the integrated restriction element 500 is part of the detector 1228. The detector 1228 is also coupled to a detector pneumatic module 1224 and an outlet 1232. The detector pneumatic module 1224 is coupled to one or more gas sources, and provides one or more pressure regulated gases to the detector 1228. The detector pneumatic module 1224 is similar to the detector pneumatic modules described above. Although shown as implemented in flame ionization detector in FIG. 12, the detector pneumatic module 1224 can be implemented with other detectors, as described above. Further, in other embodiments, the detector pneumatic module 1224 can be included within the detector 1228.

In an embodiment in which the detector is a flame ionization detector, the detector pneumatic module 1224 includes a pressure regulator 1242, a pressure regulator 1244, and a pressure regulator 1246. In an embodiment, a fuel gas, such as $H_2$, can be a supplied to the pressure regulator 1244 over connection 1262. Combustion air can be provided over connection 1264 to the pressure regulator 1246. The output of the pressure regulator 1244 is provided over connection 1269 to a restriction 1251. The output of the pressure regulator 1246 is provided over connection 1268 to a restriction 1252. The restriction 1251 and the restriction 1252 are not to be confused with the integrated restriction element 500 described herein. The restriction 1251 and the restriction 1252 are specific to the gas that is being provided to the restriction, and, in this example, provide calibrated gas flow. For example, the restriction 1251 provides a calibrated flow of combustion fuel over connection 1256 to the detector 1228. Similarly, the restriction 1252 provides a calibrated flow of air over connection 1257 to the detector 1228. A pressure sensor 1248 determines the pressure at the output of the pressure regulator 1244 and a pressure sensor 1249 determines the pressure at the output of the pressure regulator 1246.

In an embodiment, a pressure sensor 1247 is coupled to connection 1254 to sense the pressure at the exit of the chromatographic column 1226. The pressure sensor 1247 provides a pressure signal over connection 1258 to the backflush controller 150. Similarly, the pressure sensor 1248 and the pressure sensor 1249 provide pressure signals to the backflush controller 150 over connections 1259 and 1266, respectively.

The backflush controller 150 is also connected to, and controls the pressure regulator 1242, the pressure regulator 1244 and the pressure regulator 1246 individually over connection 1261. In an embodiment, because the connection 1254 is used to determine the pressure at the output of the column 1226, a restriction that would be located in line 1254 between the pressure regulator 1242 and the detector 1228 is omitted, and the pressure regulator 1242 can be set to an off, or a no-flow, position.

In an embodiment, the backflush controller 150 is optionally coupled to the flow controller 1206 over connection 1221, and optionally receives a pressure signal from the pressure sensor 1214 over connection 1222.

As described above, when it is desirable to backflush the chromatographic column 1226, a negative pressure differential condition is established in which the pressure at the exit of the chromatographic column 1226 is set higher than the pressure at the entrance of the chromatographic column 1226. This can be accomplished by increasing the pressure at the exit of the chromatographic column 1226, decreasing the pressure at the entrance of the chromatographic column 1226, or by combination of both. In an embodiment, the backflush controller 150 controls one or more pressure regulators within the detector pneumatic module 1224 and/or, optionally, the inlet pneumatic module 1202, to increase the pressure at the exit of the chromatographic column 1226 relative to the pressure at the column entrance.

In an embodiment, the backflush controller 150 controls the pressure regulator 1244 to increase the flow of, in this example, the fuel gas supplied over connection 1262, so that the pressure at the exit of the chromatographic column 1226 exceeds the pressure at the entrance to the chromatographic column 1226, thus establishing a backflush flow as described above. Alternatively, an additional gas can alternatively be supplied over connection 1241 through the pressure regulator 1242, or the gas supplied over connection 1262 can be supplied to the pressure regulator 1242, as shown using the dotted line.

In an alternative embodiment, instead of increasing the pressure at the exit of the chromatographic column 1226, the pressure at the entrance of the chromatographic column 1226 can be reduced. In this example, the backflush controller 150 receives a signal representing the output of the pressure sensor 1214 over connection 1222, and controls the flow controller 1206 to reduce the pressure at the column inlet 1211 below the pressure at the exit of the column 1226. In this manner, the pressure at the exit of the column is higher than the pressure at the entrance of the column, and backflush occurs.

Figure 13:
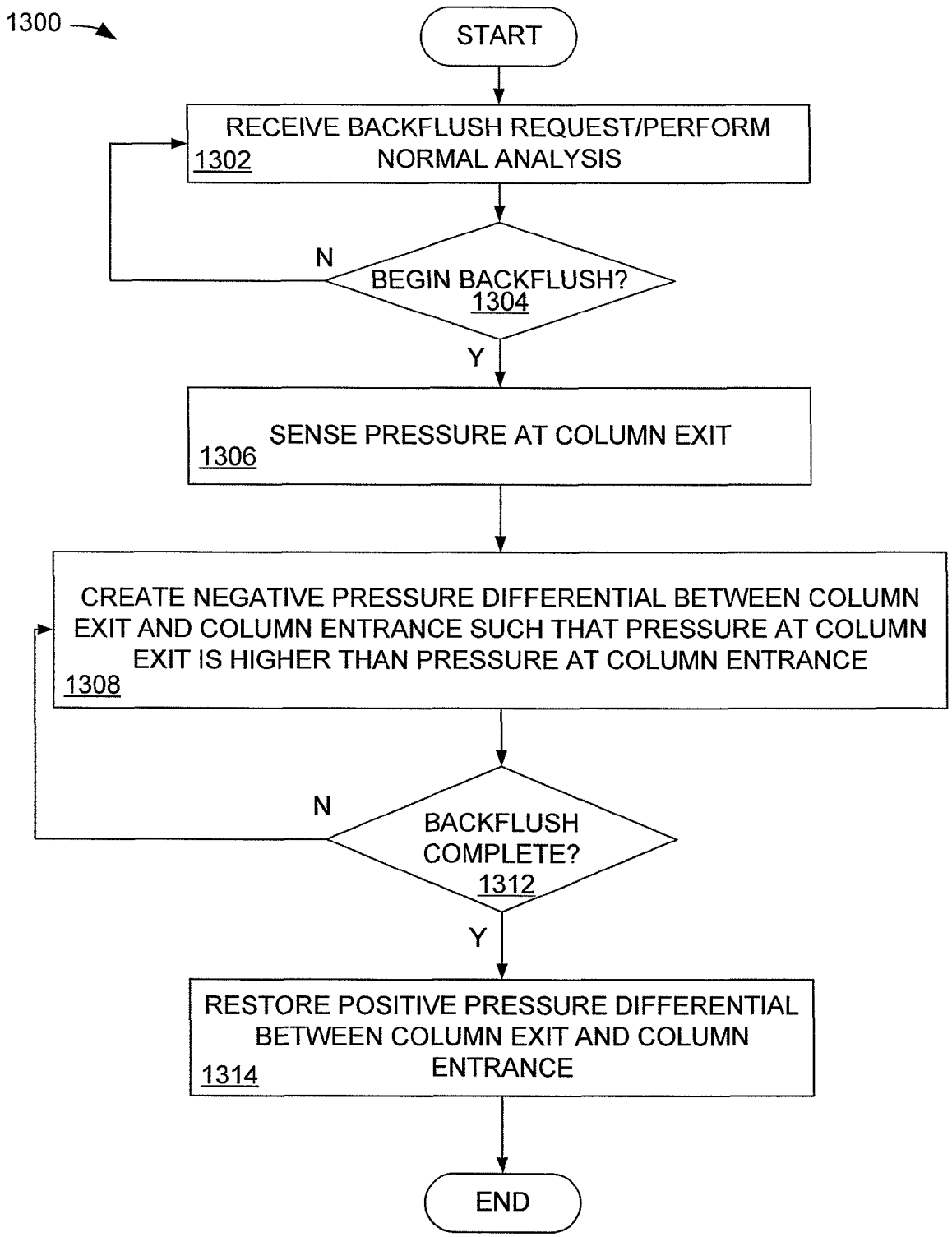
FIG. 13 is a flow chart illustrating the operation of an embodiment of the backflush controller of FIG. 12.

FIG. 13 is a flow chart illustrating an operation 1300 of an embodiment of the backflush controller described above. The backflush controller 150 (including the different embodiments of the backflush controller 250, 350 and 450, described above) can be implemented in software, firmware, or a combination of software and firmware. In an embodiment, the backflush controller 150 can be software or firmware that executes on a processor, a controller, or any control device that is located within or coupled to the gas chromatograph, and which controls the operation of the gas chromatograph. Alternatively, the backflush controller 150 can be integrated into an operating system that may be part of the gas chromatograph, or that may be peripherally coupled to the gas chromatograph.

In block 1302, a gas chromatograph awaits a backflush command. The gas chromatograph may be idle, or may be performing a normal chromatographic analysis. In block 1304, it is determined whether to begin column backflush. If column backflush is not desired, the process returns to block 1302. If column backflush is desired, then, in block 1306, the backflush controller 150 senses the pressure at the exit of the chromatographic column. In block 1308, the backflush controller 150 controls the detector pneumatic module 1224, to create a negative pressure differential between the column entrance and the column exit such that the pressure at the column exit is higher than the pressure at the column entrance. Referring briefly to FIG. 2, this can be accomplished by, for example, causing the detector pneumatic module 124 (FIG. 2) to increase the pressure at the column exit 107 above the pressure of the column entrance 105. This can be accomplished by using the backflush controller 150 to cause the detector pneumatic module 124 to adjust, control, or otherwise change the pressure at the column exit 107. The backflush controller 150 causes the detector pneumatic module 124 to create a higher relative pressure at the column exit 107 than at the column entrance 105 thus causing a backflush flow in the column 104, indicated using arrow 162, to backflush the column 104. By resisting gas flow, the orifice 504 in the integrated restriction element 500 allows the creation of a high pressure region 154 at the column exit 107. The pressure differential between the column exit 107 and the column entrance 105 can be created by increasing the pressure at the column exit 107 relative to the pressure at the column entrance 105, by lowering the pressure at the column entrance 105 relative to the pressure at the column exit 107 or a combination of both.

In block 1312, it is determined whether the backflush is complete. If the backflush is not complete, then the process returns to block 1308. If the column backflush is complete, then, in block 1314, the pressure differential at the column exit 107 and the column entrance 105 is returned to a nominal positive differential value to restore normal, forward, analysis flow.

The foregoing detailed description has been given for understanding exemplary implementations of the invention and no unnecessary limitations should be understood therefrom as modifications will be obvious to those skilled in the art without departing from the scope of the appended claims and their equivalents.

What is claimed is:

1. A detector in a gas chromatograph, comprising:
   a detector inlet configured to receive a chromatographic column, the chromatographic column having a column entrance and a column exit, the column exit coupled to the detector inlet;
   a restriction, wherein the restriction located to receive an output of the chromatographic column;
   at least one pressure regulated gas source provided for normal gas chromatograph operation and arranged to provide at least one gas to a location between the restriction and the column exit; and a backflush controller coupled to the pressure regulated gas source, the backflush controller configured to control a pressure differential between the column exit and the column entrance such that the at least one gas backflushes the chromatographic column when a pressure at the column exit exceeds a pressure at the column entrance.

2. The detector of claim 1, further comprising a jet in the detector inlet, wherein the restriction is integrated in the jet.

3. The detector of claim 1, further comprising a guide tube in the detector inlet, wherein the restriction is integrated in the guide tube.

4. The detector of claim 1, wherein the restriction is located at the detector inlet.

5. The detector of claim 1, wherein the restriction is located at an outlet of the detector.

6. The detector of claim 1, further comprising a pressure regulator connected with the column entrance.

7. The detector of claim 1, wherein the restriction is an axial orifice.

8. The detector of claim 7, wherein the axial orifice has a diameter ranging between 5 and 70 micrometers ($\mu m$).

9. The detector of claim 1, wherein the restriction is a linear restriction.

10. The detector of claim 1, wherein the restriction is a porous frit.

11. A system for backflushing a column in a gas chromatograph, comprising:

an inlet pneumatic module coupled to a chromatographic inlet;

a chromatographic column coupled to the chromatographic inlet, the chromatographic column having a column entrance and a column exit, the column exit coupled to an inlet of a detector, the detector comprising:
a restriction, wherein the restriction located to receive an output of the chromatographic column;
a detector pneumatic module having at least one pressure regulated gas source provided for normal gas chromatograph operation and arranged to provide at least one pressure regulated gas to a location between the restriction and the column exit; and
a backflush controller coupled to the detector pneumatic module, the backflush controller configured to control a pressure differential between the column exit and the column entrance such that the at least one gas backflushes the chromatographic column when a pressure at the column exit exceeds a pressure at the column entrance.

12. The system of claim 11, further comprising a jet in the detector inlet, wherein the restriction is integrated in the jet.

13. The system of claim 11, further comprising a guide tube in the detector inlet, wherein the restriction is integrated in the guide tube.

14. The system of claim 11, wherein the restriction is located at the inlet to the detector.

15. The system of claim 11, wherein the restriction is located at an outlet of the detector.

16. The system of claim 11, wherein the backflush controller causes the detector pneumatic module to increase a pressure of the pressure regulated gas at the column exit to create a pressure differential between the column exit and the column entrance.

17. The system of claim 11, wherein the backflush controller causes the inlet pneumatic module to decrease a pressure at the column entrance to create a pressure differential between the column exit and the column entrance.

18. The system of claim 11, wherein the restriction is an axial orifice.

19. The system of claim 18, wherein the axial orifice has a diameter ranging between 5 and 70 micrometers ($\mu m$).

20. The system of claim 11, wherein the restriction is a porous frit.

* * * * *